(12) United States Patent
Tegg

(10) Patent No.: US 7,749,247 B2
(45) Date of Patent: *Jul. 6, 2010

(54) TISSUE PUNCTURE CLOSURE DEVICE WITH COILED AUTOMATIC TAMPING SYSTEM

(75) Inventor: Troy Tegg, Elk River, MN (US)

(73) Assignee: St. Jude Medical Puerto Rico, LLC, Caguas, PR (US)

( * ) Notice: Subject to any disclaimer, the term of this patent is extended or adjusted under 35 U.S.C. 154(b) by 1250 days.

This patent is subject to a terminal disclaimer.

(21) Appl. No.: 11/197,382

(22) Filed: Aug. 4, 2005

(65) Prior Publication Data

US 2007/0032823 A1 Feb. 8, 2007

(51) Int. Cl.
*A61B 17/08* (2006.01)

(52) U.S. Cl. .................. 606/213; 606/232; 606/139

(58) Field of Classification Search ............... 606/139, 606/144, 232, 93–95, 213; 112/169
See application file for complete search history.

(56) References Cited

U.S. PATENT DOCUMENTS

| | | | |
|---|---|---|---|
| 4,744,364 A | 5/1988 | Kensey et al. | |
| 4,890,612 A | 1/1990 | Kensey et al. | |
| 5,021,059 A | 6/1991 | Kensey et al. | |
| 5,222,974 A | 6/1993 | Kensey et al. | |
| 5,282,827 A | 2/1994 | Kensey et al. | |
| 5,290,310 A | 3/1994 | Makower et al. | |
| 5,411,520 A | 5/1995 | Nash et al. | |
| 5,441,517 A | 8/1995 | Kensey et al. | |
| 5,531,759 A * | 7/1996 | Kensey et al. | 606/213 |
| 5,545,178 A | 8/1996 | Kensey et al. | |
| 5,662,681 A | 9/1997 | Nash et al. | |
| 5,707,393 A | 1/1998 | Kensey et al. | |
| 5,779,719 A | 7/1998 | Klein et al. | |
| 5,861,004 A | 1/1999 | Kensey et al. | |
| 5,935,147 A | 8/1999 | Kensey et al. | |
| 5,993,467 A * | 11/1999 | Yoon | 606/147 |
| 6,007,563 A | 12/1999 | Nash et al. | |
| 6,045,569 A | 4/2000 | Kensey et al. | |
| 6,086,607 A | 7/2000 | Cragg | |
| 6,162,192 A | 12/2000 | Cragg | |
| 6,425,911 B1 | 7/2002 | Akerfeldt et al. | |
| 7,131,979 B2 * | 11/2006 | DiCarlo et al. | 606/144 |
| 7,250,057 B2 * | 7/2007 | Forsberg | 606/213 |
| 2003/0060846 A1 | 3/2003 | Egnelov et al. | |
| 2005/0085851 A1 | 4/2005 | Fiehler et al. | |
| 2006/0029674 A1* | 2/2006 | Sever et al. | 424/486 |
| 2006/0229673 A1* | 10/2006 | Forsberg | 606/232 |

(Continued)

FOREIGN PATENT DOCUMENTS

WO  WO 0078226 A1 * 12/2000

*Primary Examiner*—Julian W Woo
*Assistant Examiner*—Alexander Orkin
(74) *Attorney, Agent, or Firm*—Holland & Hart

(57) ABSTRACT

A method and apparatus for sealing a puncture or incision formed percutaneously in a tissue with an anchor, a sealing plug and a filament or other mechanism connecting the anchor and sealing plug. The method and apparatus provide for automatic tamping and/or cinching of the sealing plug when the apparatus is withdrawn from the puncture site. The automatic tamping and/or cinching is facilitated by a coil transducing a motive force generated by the withdrawal of the apparatus into a tamping and/or cinching force.

19 Claims, 9 Drawing Sheets

U.S. PATENT DOCUMENTS

2006/0265006 A1* 11/2006 White et al. ................. 606/232
2006/0265007 A1* 11/2006 White et al. ................. 606/232
2007/0255314 A1* 11/2007 Forsberg ..................... 606/213
2008/0071311 A1* 3/2008 White et al. ................. 606/232

* cited by examiner

TISSUE PUNCTURE CLOSURE DEVICE WITH COILED AUTOMATIC TAMPING SYSTEM

FIELD OF THE INVENTION

This invention relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,963; 6,090,130; and 6,045,569 and related patents that are hereby incorporated by reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a tamping tube. The tamping procedure cannot commence until the device sheath (within which the tamping tube is located) has been removed so as to expose the tamping tube for manual grasping. Under certain conditions, removal of the sheath prior to tamping the sealing plug may cause the sealing plug itself to be displaced proximally from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present invention meets the above-described needs and others. Specifically, the present invention provides methods and systems for closing internal tissue punctures. However, unlike prior systems, the present invention provides automatic tamping to a sealing plug as the closure device is retracted. In addition, the present invention allows the automatic tamping system to disengage, facilitating full retraction of the closure device and easy separation of the sealing plug from the remainder of the closure device.

In one of many possible embodiments, the present invention provides an apparatus comprising a tissue puncture closure device, the tissue puncture closure device comprising an anchor, a sealing plug, a connector slidingly attaching the sealing plug to the anchor, and a coil operatively connected to the sealing plug for automatically tamping the sealing plug toward the anchor. The tissue puncture closure device may further comprise a tamping tube disposed adjacent to the sealing plug, such that the tamping tube is driven by the coil to tamp the sealing plug. The tissue puncture closure device may further comprise a housing, a block disposed in the housing and receptive of at least a portion of the coil, and a driving plate adjacent to the coil. The block may comprise a curved channel, and the driving plate may comprise a drive pin extending into the curved channel adjacent to a first end of the coil.

According to some embodiment, the apparatus may comprise a spool connected to the driving plate, where a portion of the filament is wound around the spool. The spool may be connected by a releasable clutch to the driving plate.

Some embodiments of the block may comprise a spiraled channel receptive of at least a portion of the coil, and the driving plate may comprise a drive pin extending into the spiraled channel adjacent to a first end of the coil. The driving plate may comprise a radially floating, angularly stable drive pin extending into the spiraled channel adjacent to the first end of the coil. The driving plate may comprise a radially compliant, angularly stable drive pin extending into the spiraled channel adjacent to the first end of the coil.

According to some embodiments, the block disposed in the housing comprises a curved channel portion leading to a straight channel portion, the curved and straight channel portions receptive of at least a portion of the coil.

According to some embodiments, the coil is driven by a disengagable automatic driving mechanism to tamp the sealing plug, and the selectably disengagable automatic driving mechanism comprises a transducer for effecting a tamping force on the sealing plug via the coil upon withdrawal of the closure device from the tissue wall puncture.

Another aspect of the invention provides a tissue puncture closure device for partial insertion into and sealing of a tissue puncture in an internal tissue wall accessible through a percutaneous incision. The device comprises an anchor for disposition on a distal side of the internal tissue wall, a sealing plug for disposition on a proximal side of the internal tissue wall, a filament connected to and anchored at a distal end to the anchor and sealing plug for slidably cinching the anchor and sealing plug together about the tissue puncture, where the sealing plug is slidably disposed on the filament proximal to the anchor. The device also includes a tamping device disposed on the filament for driving the sealing plug along the filament distally towards the anchor, a storage spool onto which a proximal end of the filament is wound, a driving plate connected to the storage spool, and a coil operatively connected to the driving plate for providing a tamping force to the sealing plug. The device may further comprise a housing, and a block disposed in the housing comprising a curved channel receptive of at least a portion of the coil, where the driving plate is rotatably attached to the block, and the driving plate comprises a drive pin extending into the curved channel adjacent to a first end of the coil. The block disposed in the housing may comprise a spiraled channel receptive of at least a portion of the coil, and the driving plate may comprise a disk rotatably attached to the block, a slit in the disk, and a radially flexible cantilevered finger in the disk having a drive pin extending laterally into the spiraled channel at a first end of the coil. According to some embodiments the coil also comprises the tamping device.

According to some embodiments, withdrawal of the closure device from the tissue puncture with the anchor bearing against the internal tissue wall unwinds the filament from the storage spool. Further, the storage spool may rotate the driving plate, and the driving plate may drive the coil to directly or indirectly provide a tamping force to the sealing plug.

Another aspect of the invention provides a method of sealing a tissue puncture in an internal tissue wall accessible through a percutaneous incision. The method comprises withdrawing a closure device from the tissue puncture, automatically transducing a motive force generated by withdrawal of the closure device in a first direction to a cinching or tamping force from a coil in a second direction, and disabling the tamping force in the second direction. The cinching or tamping force in the second direction may be applied to a sealing plug.

The method may further comprise transferring the motive force to a driving plate, and driving the coil with the driving plate. The coil may abut a tamping tube that is slidingly disposed about a filament, and the filament may be slidingly connected to the sealing plug. The transferring may further comprise automatically unwinding the filament from a spool by deploying an anchor attached to the filament inside the tissue puncture, and withdrawing the closure device from the tissue puncture. The transferring may also comprises driving a pin extending from the driving plate along a channel holding the coil via the unwinding. The disabling may comprise disconnecting the spool from the driving plate.

Another method of sealing a tissue puncture in an internal tissue wall accessible through a percutaneous incision may comprise providing a tissue puncture closure device comprising a filament connected at its distal end to an anchor and to a sealing plug located proximal of the anchor for disposition and anchoring about the tissue puncture, the tissue puncture closure device also comprising a coiled automatic tamping device, inserting the tissue puncture closure device into the percutaneous incision, deploying the anchor into the tissue puncture, at least partially withdrawing the closure device from the percutaneous incision, automatically tamping the sealing plug toward the anchor upon withdrawal of the closure device from the internal tissue wall puncture with the coiled automatic tamping device, disengaging the coiled automatic tamping device, retracting the tissue puncture closure device, exposing the filament, cutting the filament, and leaving the anchor and the sealing plug at the tissue puncture. The coiled automatic tamping device may comprise a block comprising a curved channel receptive of at least a portion of a coil, a driving plate rotatably attached to the block, the driving plate comprising a drive pin extending into the curved channel adjacent to a first end of the coil, and a spool connected by a releasable clutch to the driving plate, where a portion of the filament is wound around the spool.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1:
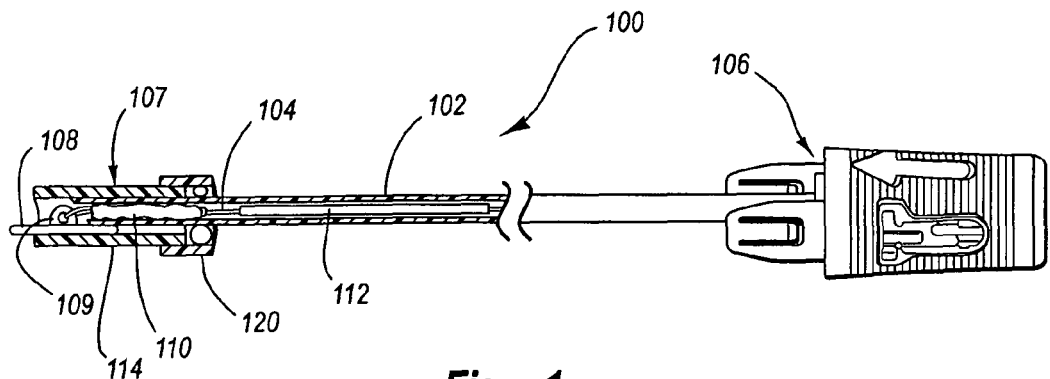
FIG. 1 is a partial cut-away view of a tissue closure device according to the prior art.

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is difficult to eject from the sealing device and may not properly seat against an exterior situs of the arteriotomy. If the plug does not seat properly against the arteriotomy, there is a potential for elongated bleeding. The present invention describes methods and apparatus that facilitate sealing plug ejection and proper placement of the sealing plug. While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

As used in this specification and the appended claims, the term "tamp" or "tamping" is used broadly to mean packing down by one or a succession of blows or taps or smooth, steady pressure, but not by excessive force. A "coil" is an object arranged in a curve, spiral, ring or winding capable of supporting a compressive load. A "spool" is a cylinder or other device on which something else is at least partially wound. A "tube" is an elongated device with a passageway. The passageway may be enclosed or open (e.g. a trough). A "lumen" refers to any open space or cavity in a bodily organ, especially in a blood vessel. "Slidingly mounted" means movable relative to an appropriate support. "Free floating" means able to move freely according to at least one degree of freedom. "Free floating" movement is not necessarily unlimited, and may include free movement only within a specified range. "Transduce" means to convert a force or other input energy in one form into output energy or forces of another form or direction. The term "effecting" means producing an outcome, achieving a result, or bringing about. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
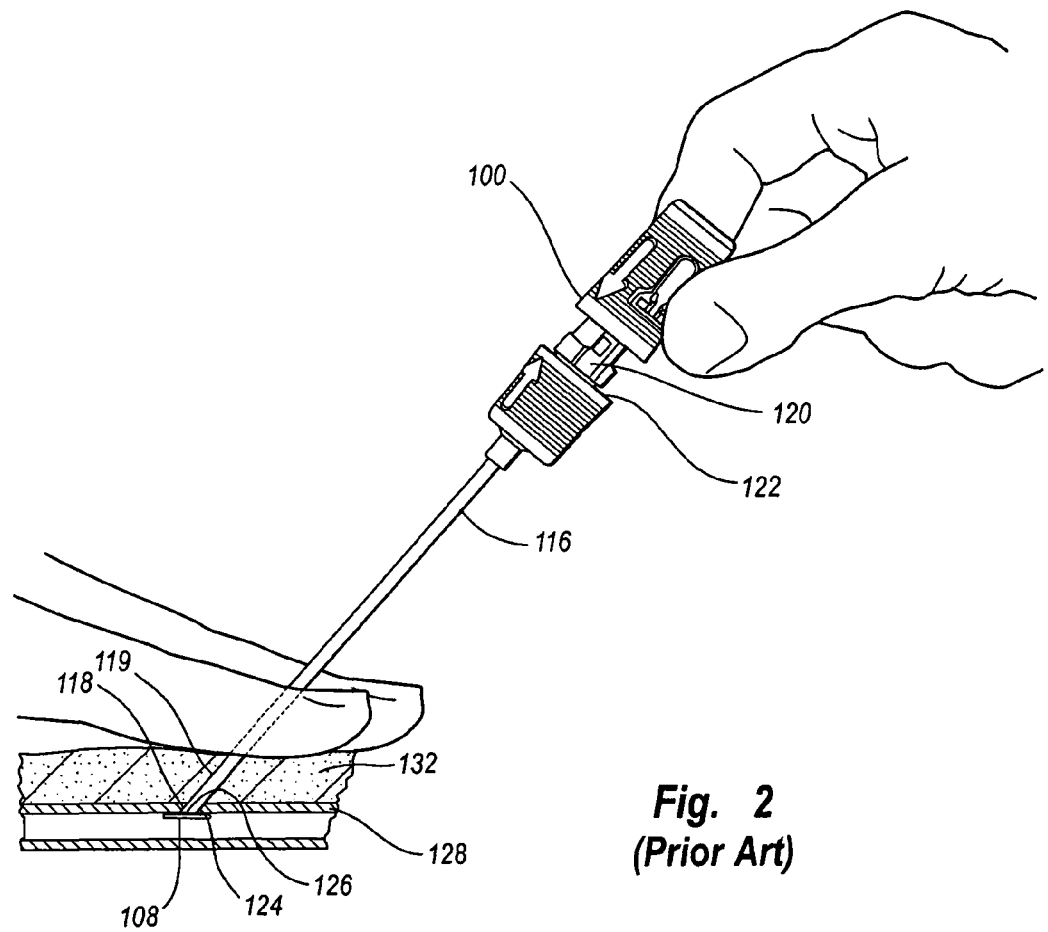
FIG. 2 is a side view of the tissue closure device of FIG. 1 engaged with an artery according to the prior art.
Figure 3:
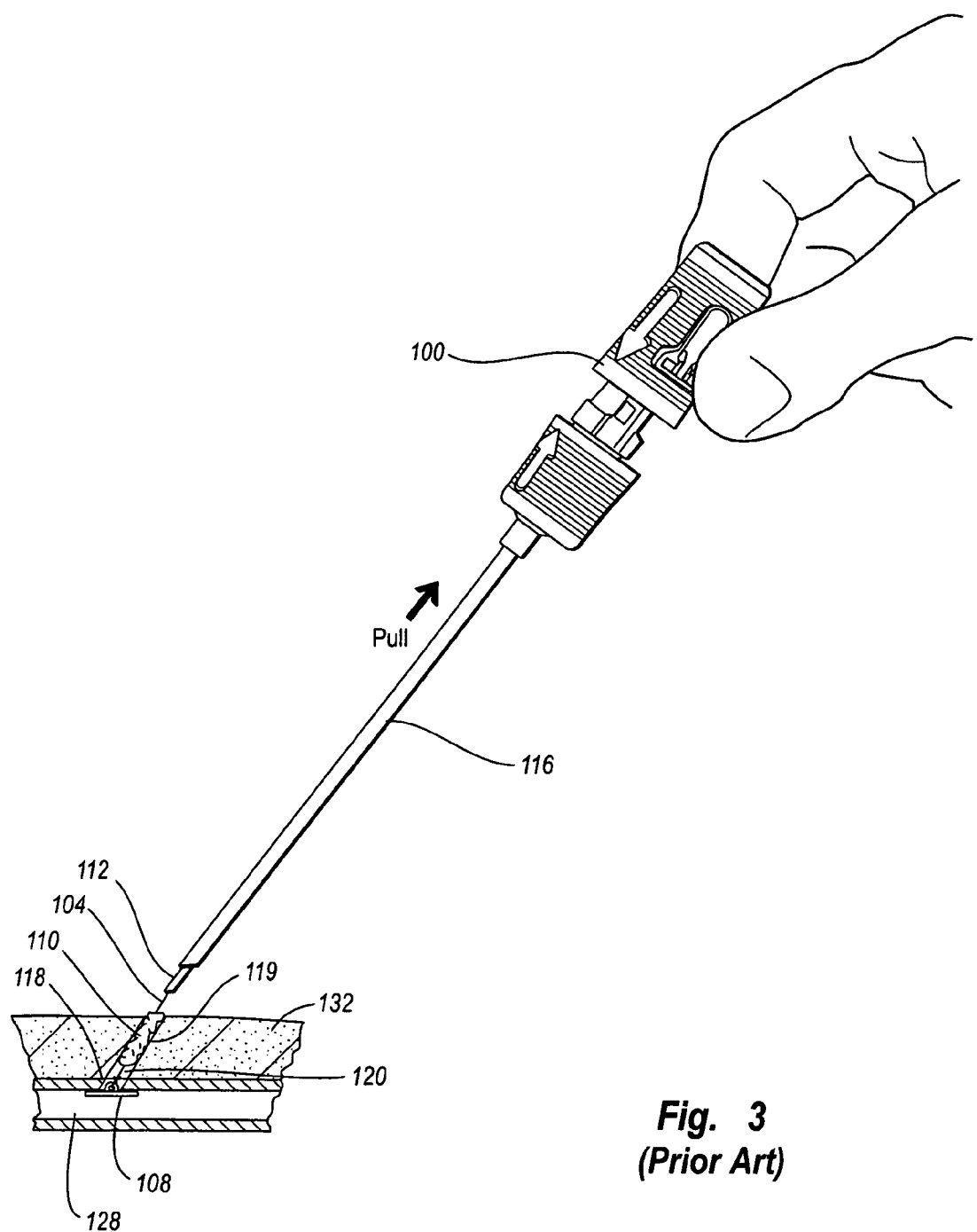
FIG. 3 is a side view of the tissue closure device of FIG. 1 being withdrawn from an artery according to the prior art to deploy a collagen sponge.
Figure 4:
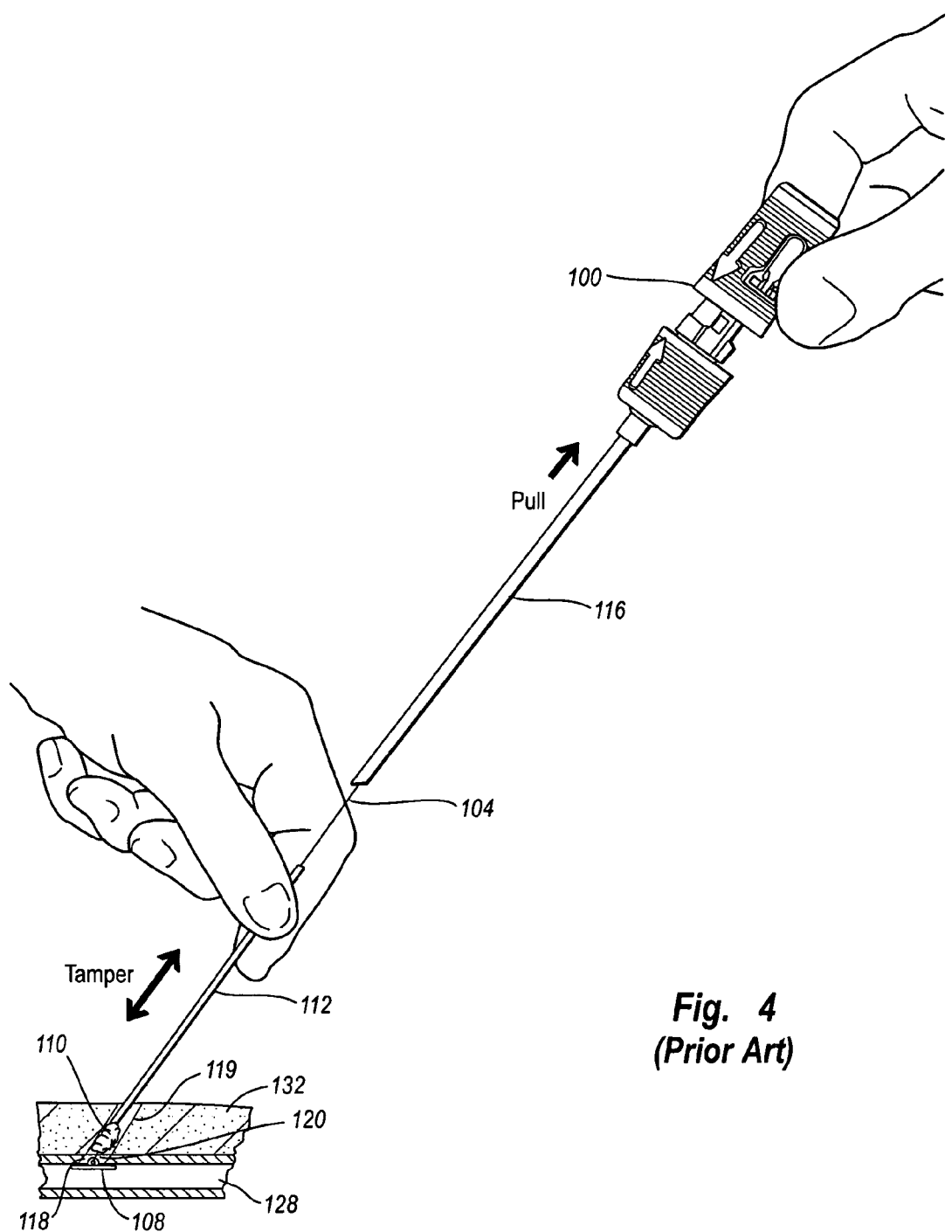
FIG. 4 is a side view of the tissue closure device of FIG. 1 illustrating tamping of the collagen sponge according to the prior art.

The flush arrangement of the anchor 108 and carrier tube 102 allows the anchor 108 to be inserted into a procedure sheath such as insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, ejecting the collagen pad 110 from the carrier tube 102 into the incision tract 119 and exposing the tamping tube 112. With the tamping tube 112 fully exposed as shown in FIG. 4, the collagen pad 110 is manually tamped, and the anchor 108 and collagen pad 110 are cinched together and held in place with the self-tightening slip-knot on the suture 102. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

Using the typical tissue puncture closure device 100 described above, however, it may be difficult to tamp of the collagen pad 110. Tamping cannot commence until the sheath 116 has been removed so as to expose the tamping tube 112 for manual grasping. Under certain conditions, removal of the sheath 116 prior to tamping the collagen pad 110 causes the collagen pad 110 to retract or displace proximally from the tissue puncture 118, creating an undesirable gap 120 between the collagen pad 110 and the puncture 118. The gap 120 may remain even after tamping as shown in FIG. 4, and sometimes results in only a partial seal and bleeding from the tissue puncture 118.

Therefore, the present specification describes an apparatus such as a tissue puncture closure device that is capable of automatically tamping the sealing plug upon withdrawal of the tissue puncture closure device from the tissue puncture site. The mechanism for automatically driving the sealing plug may comprise a coil operatively connected to the sealing plug, and the mechanism may be selectably disengagable.

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5A-5G, an apparatus, for example a tissue wall puncture closure device 200, is shown according to one embodiment of the present invention. The closure device 200 is shown in an assembly view in FIG. 5A. FIGS. 5B-5G illustrate the closure device 200 assembled and inserted through a procedure sheath 216 and into a lumen 232. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the closure device 200 according to principles of the present invention.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit 209.

Figure 5A:
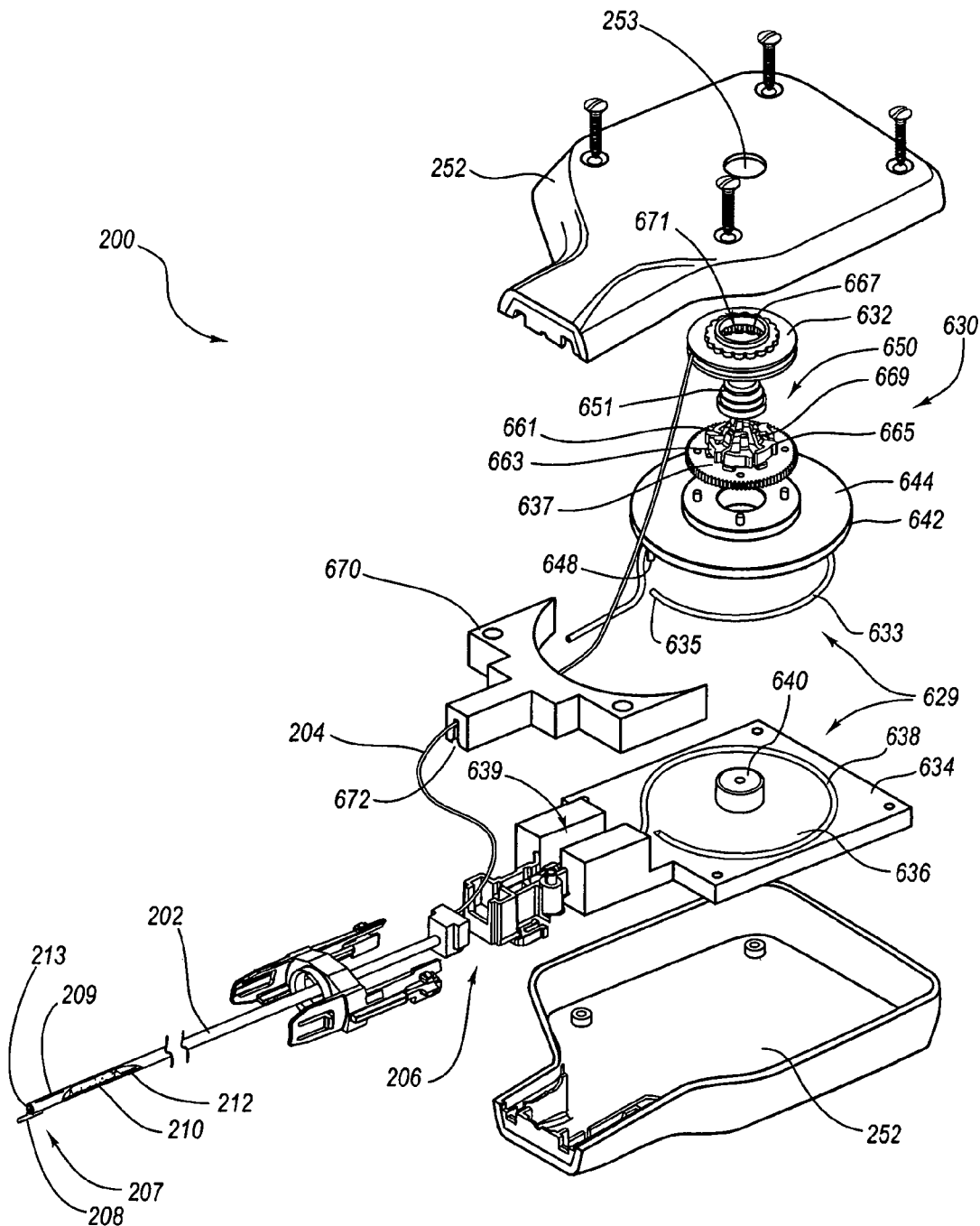
FIG. 5A is a perspective assembly view of a tissue puncture closure device with an automatic tamping or driving mechanism according to one embodiment of the present invention.
Figures 5B, 5C:
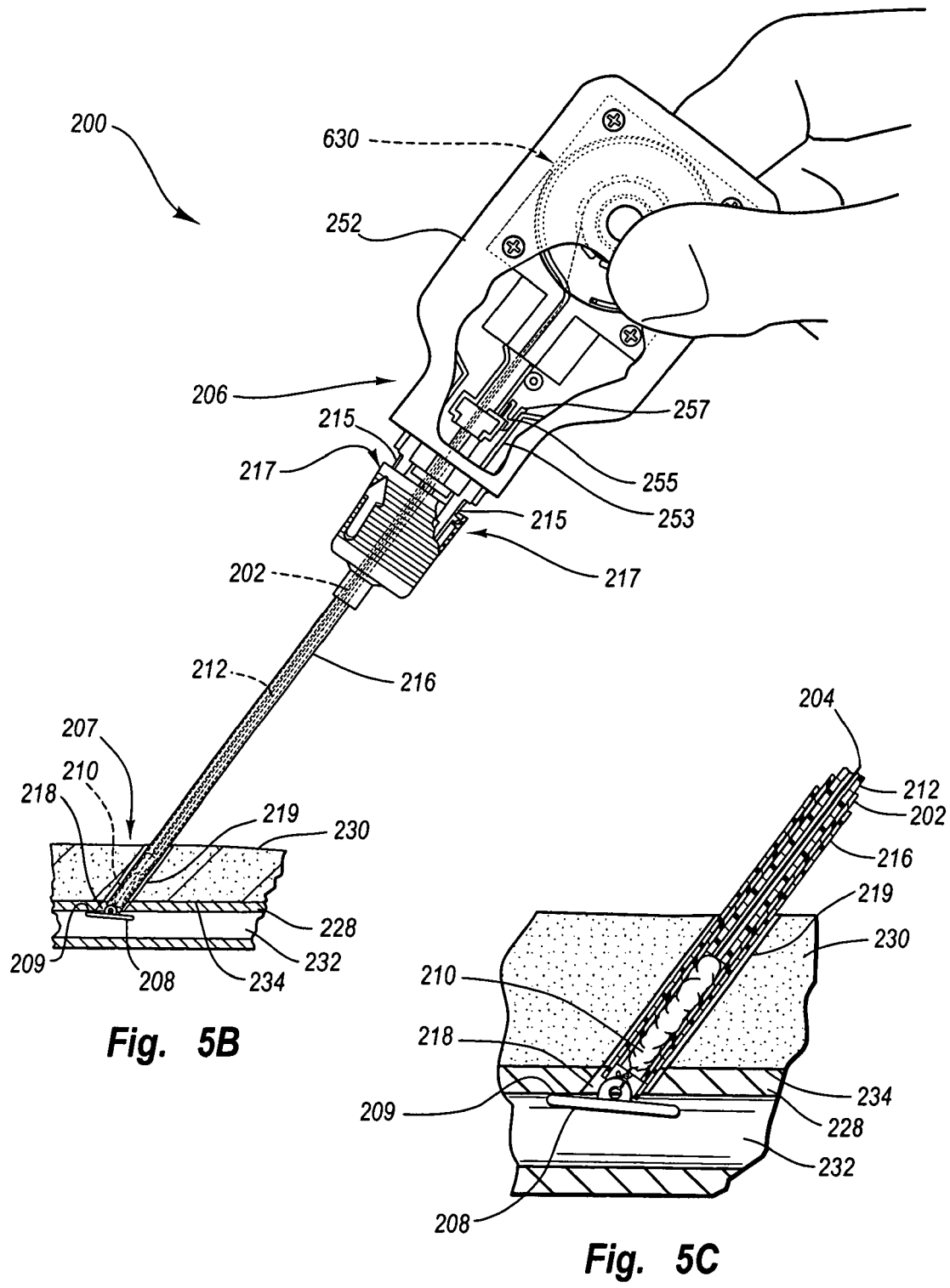
FIG. 5B is a side view of the tissue closure device of FIG. 5A inserted through a procedure sheath and shown engaged with an artery in a first position according to one embodiment of the present invention.
FIG. 5C is a detailed inset of FIG. 5B.

The carrier tube 202 may be made of plastic or other material and is designed for insertion through the procedure sheath 216 (FIG. 5B). The procedure sheath 216 (FIG. 5B) is designed for insertion through a percutaneous incision 219 (FIG. 5B) in a tissue layer 230 (FIG. 5B) and into the lumen 232 (FIG. 5B). According to FIGS. 5B-5G, the lumen 232 comprises an interior portion of a femoral artery 228.

At the distal end portion 207 of the carrier tube 202 there is an anchor 208 and a sealing plug 210. The anchor 208 of the present embodiment is an elongated, stiff, low-profile member arranged to be seated inside the artery 228 (FIG. 5B) against an artery wall 234 (FIG. 5B) contiguous with a puncture 218 (FIG. 5B). The anchor 208 is preferably made of a biologically resorbable polymer. The sealing plug 210 (FIG. 5B) is formed of a compressible sponge, foam, or fibrous mat made of a non-hemostatic biologically resorbable material such as collagen, and may be configured in any shape so as to facilitate sealing the tissue puncture 218 (FIG. 5B).

The sealing plug 210 and anchor 208 are connected to one another by a connector such as a filament or suture 204 that is also biologically resorbable. The anchor 208, the sealing plug 210, and the suture 204 are collectively referred to as the "closure elements" below. As shown in FIG. 5A, the anchor 208 is initially arranged adjacent to and exterior of the distal end portion 207 of the carrier tube 202, while the sealing plug 210 (FIG. 5B) is initially disposed within the carrier tube 202. The anchor 208 is shown nested in its low profile configuration along the carrier tube 202 to facilitate insertion into the lumen 232 (FIG. 5B) in FIG. 5A, and deployed with a first surface 236 abutting the artery wall 234 in FIGS. 5B-5G. The suture 204 extends distally from the first end portion 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210. The anchor 208 and the sealing plug 210 sandwich and lock the anchor and plug together, sealing the tissue puncture 218.

The carrier tube 202 may house a tamping device, such as a tamping tube 212, for advancing the sealing plug 210 along the suture 204 and toward the anchor 208. The tamping tube 212 is shown located partially within the carrier tube 202 and proximal of the sealing plug 210. The tamping tube 212, however, also extends through a handle or housing 252 of the closure device 200. The tamping tube 212 is preferably an elongated tubular or semi-tubular member that may be rigid or flexible and formed of any suitable material. For example, according to one embodiment, the tamping tube 212 is made of polyurethane. The suture 204 extends through at least a portion of the tamping tube 212. For example, as shown in FIGS. 5A-5G, the suture 204 extends along the tamping tube 212 between the first and second end portions 206, 207. However, the suture 204 is not directly connected to the tamping tube 212. Accordingly, the suture 204 and the tamping tube 212 may slide past one another.

According to the embodiment of FIGS. 5A-5G, the suture 204 attaches to an automatic tamping assembly. The automatic tamping assembly may include an automatic driving mechanism 630 or other transducer and the tamping tube 212. The automatic driving mechanism 630 is located within the housing or handle 252 at the first end portion 206 of the closure device 200. Embodiments of the automatic driving mechanism 630 are described in detail below with reference to FIGS. 6-8 and may be selectively disengagable.

In practice, the carrier tube 202 of the closure device 200 (containing the closure elements described above) is inserted into the insertion sheath 216, which is already inserted within the artery 228 (FIGS. 5B-5C). As the closure device 200 and the associated closure elements are inserted into the procedure sheath 216, the anchor 208 passes through and out of the distal end of the procedure sheath 216 and is inserted into the artery lumen 232. As mentioned above and shown in FIG. 5A, the anchor 208 is initially arranged substantially flush with the carrier tube 202 to facilitate insertion of the anchor 208 through the percutaneous incision 219 and into the lumen 232.

After the anchor 208 passes out of the distal end of the procedure sheath 216, however, it tends to deploy or rotate to the position shown in FIGS. 5B-5C. The closure device 200 may also be partially withdrawn from the insertion sheath 216, catching the anchor 208 on the distal end of the insertion sheath 216 and rotating it to the position shown in FIGS. 5B-5C. However, the closure device 200 preferably includes a pair of biased fingers 215 that are lockingly received by a matching pair of recesses 217 in the procedure sheath 216. The locking arrangement between the biased fingers 215 and matching recesses 217 may fix the position of the handle 252 relative to the procedure sheath 216.

Following deployment of the anchor 208, the handle 252 and the insertion sheath 216 are withdrawn together. Withdrawing the handle 252 causes the anchor 208 to anchor itself within the artery 228 against the artery wall 234. With the anchor 208 anchored within the artery 228 at the puncture site 218, further retraction of the handle 252 and insertion sheath 216 tends to pull the sealing plug 210 out from the distal end portion 207 of the carrier tube 202, thereby depositing the plug 210 within the incision or puncture tract 219. The slit 209 (FIG. 5A) in the carrier tube 202 allows the distal end portion 207 of the carrier tube to flex or open, facilitating ejection of the sealing plug 210.

Figures 5D, 5E:
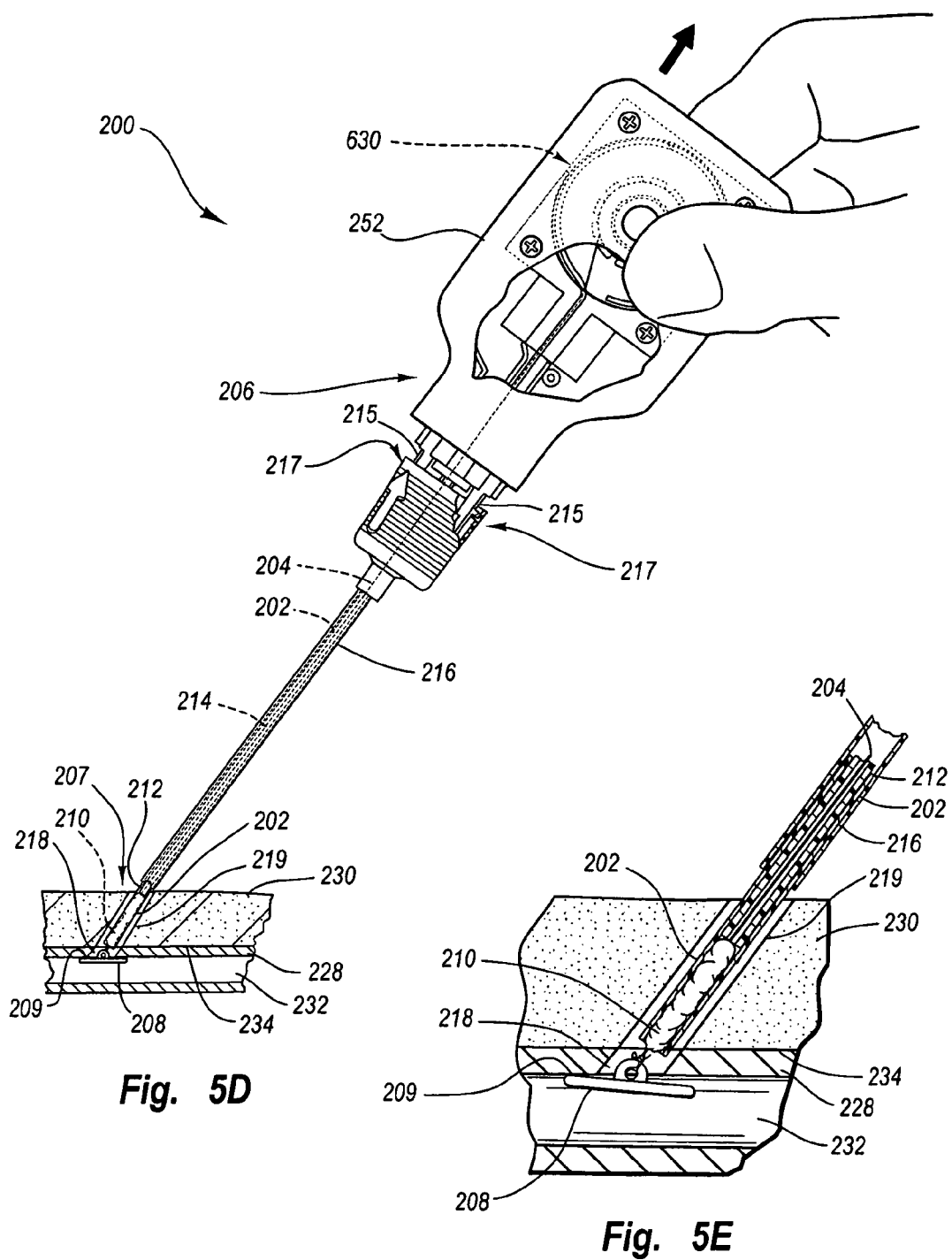
FIG. 5D is a side view of the tissue closure device of FIG. 5A shown engaged with an artery in a second position and being retracted according to one embodiment of the present invention.
FIG. 5E is a detailed inset of FIG. 5D.

Referring to FIGS. 5D-5E, the distal end portion 207 of the carrier tube 202 is exposed (within the incision tract 219) as the handle 252 and the procedure sheath 216 are retracted. The carrier tube 202 may retain its position relative to the puncture 218 until the handle 252 and the procedure sheath 216 have been retracted a predetermined distance. Relative movement between the handle 252/procedure sheath 216 and the carrier tube 202 may facilitated by a sliding mount arrangement between the automatic driving mechanism 630 and the handle 252. However, according to some embodiments the automatic driving mechanism 630 is fixed to the handle 252.

As shown by the combination of FIGS. 5B-5G, the automatic driving mechanism 630 (which is attached to the carrier tube 202) may be free floating or displaceable and slides relative to the handle 252 as the handle 252 and the procedure sheath 216 are retracted. However, the automatic driving mechanism 630 may be initially held in a first position relative to the handle 252 as shown in FIG. 5B. For example, as shown in FIG. 5B, the automatic driving mechanism 630 may comprise a temporary holder such as a stowage detent 255 slidingly mounted in a track. The track is shown in FIG. 5B as a webbing track 253. The webbing track 253 is disposed in the handle 252. The stowage detent 255 may include a finger 257 with a protrusion to at least temporarily hold the automatic driving mechanism 630 in the first position shown in FIG. 5B, and prevent premature sliding within the handle 252.

Although the finger 257 tends to hold or temporarily lock the automatic driving mechanism 630 in the first position shown in FIG. 5B, the finger 257 releases when a sufficient predetermined force is applied between the handle 252 and the automatic driving mechanism 630. For example, with the anchor 208 deployed, a retraction force provided by a user to the handle 252 causes the finger 257 to deflect inward and release. Thereafter, the finger 257 provides very little resistance to sliding movement between the automatic driving mechanism 630 and the handle 252. Accordingly, retraction of the handle 252 may retract the procedure sheath 216 (which is fixedly connected to the handle 252), but the automatic driving mechanism 630 and the carrier tube 202 may slide relative to the handle 252 and therefore remain in position with respect to the puncture 218 as shown in FIG. 5D. The automatic driving mechanism 630 may slide a predetermined distance with respect to the handle 252 until the automatic driving mechanism 630 reaches a stop. The predetermined distance may be at least long enough to fully expose the slit 209 (FIG. 5A) in the carrier tube 202.

Figures 5F, 5G:
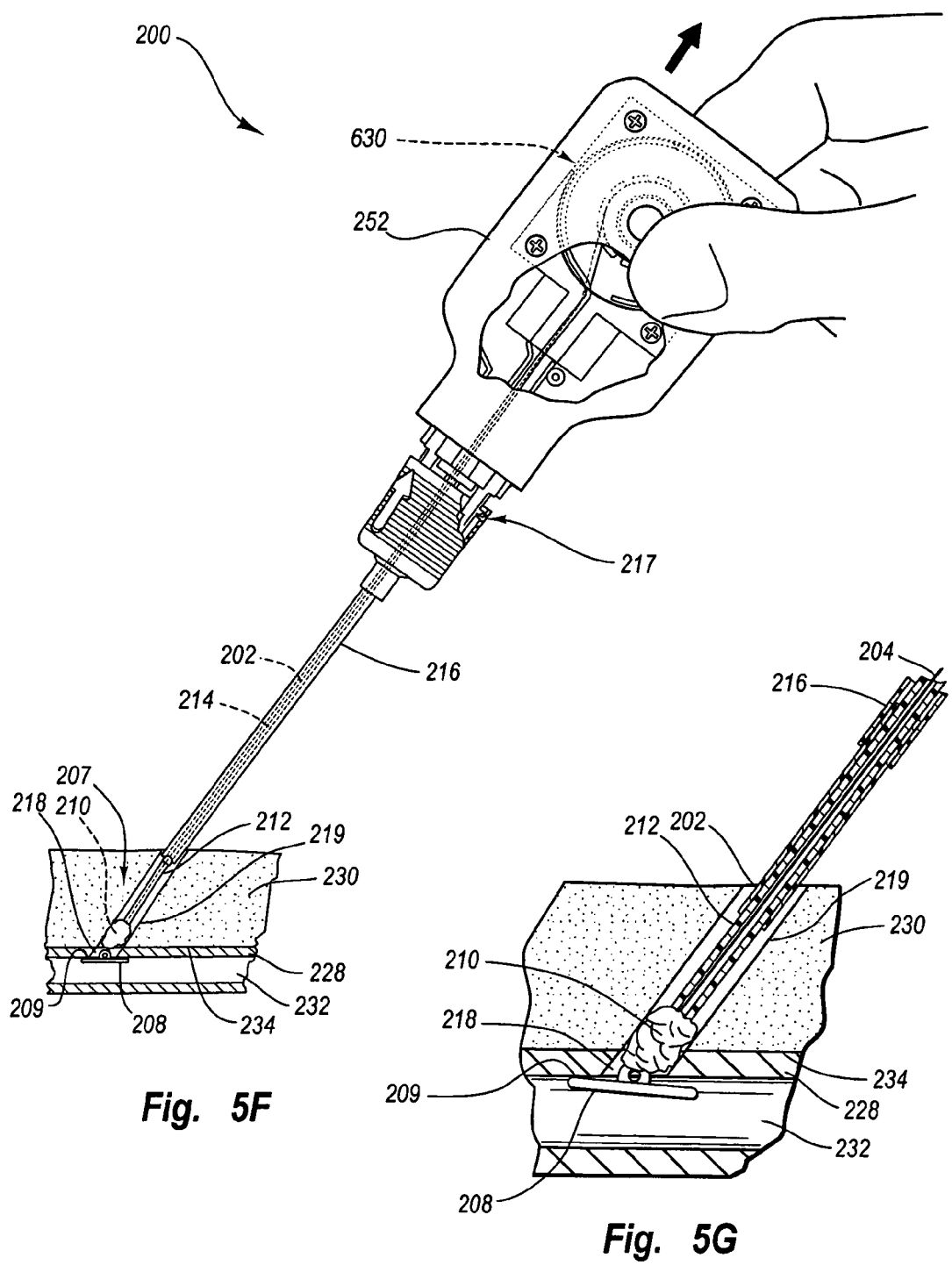
FIG. 5F is a side view of the tissue closure device of FIG. 5A shown engaged with an artery in a third position tamping a sealing plug according to one embodiment of the present invention.
FIG. 5G is a detailed inset of FIG. 5F.

When the automatic driving mechanism 630 reaches the stop, further retraction of the handle 252 withdraws the carrier tube 202 as well, ejecting and tamping the sealing plug 210 automatically as shown in FIGS. 5F-5G. Unlike previous closure devices that require a separate, manual tamping procedure following the deposition of the sealing plug 210, the closure device 200 of the present invention automatically tamps the sealing plug 210. The sealing plug 210 may be tamped while the carrier tube 202 is being withdrawn, reducing or eliminating any gaps that may otherwise occur between the sealing plug 210 and the puncture 218 in the femoral artery 228.

In addition, by placing tension on or pulling the suture 204 away from the puncture tract 219, the suture 204 may cinch and lock (with a slip knot or the like) together the anchor 208 and the sealing plug 210, sandwiching the artery wall 234 between the anchor 208 and sealing plug 210. The force exerted by the tamping tube 212 and the cinching together of the anchor 208 and sealing plug 210 by the filament 204 also causes the sealing plug 210 to deform radially outward within the puncture tract 219 and function as an anchor on the proximal side of the tissue puncture site 218 as shown in FIGS. 5F-5G.

The tamping tube 212 is automatically driven toward the sealing plug 210 by the automatic driving mechanism 630. One embodiment of the automatic driving mechanism 630 is shown in detail in FIGS. 5A and 6. The automatic driving mechanism 630 may comprise a coil assembly 629 and may be selectably disengageable. According to the embodiment of FIGS. 5A and 6, once the automatic driving assembly 630 contacts the stop, further retraction of the closure device 200 automatically effects tamping of the sealing plug 210 (see FIGS. 5F-5G).

Figure 6:
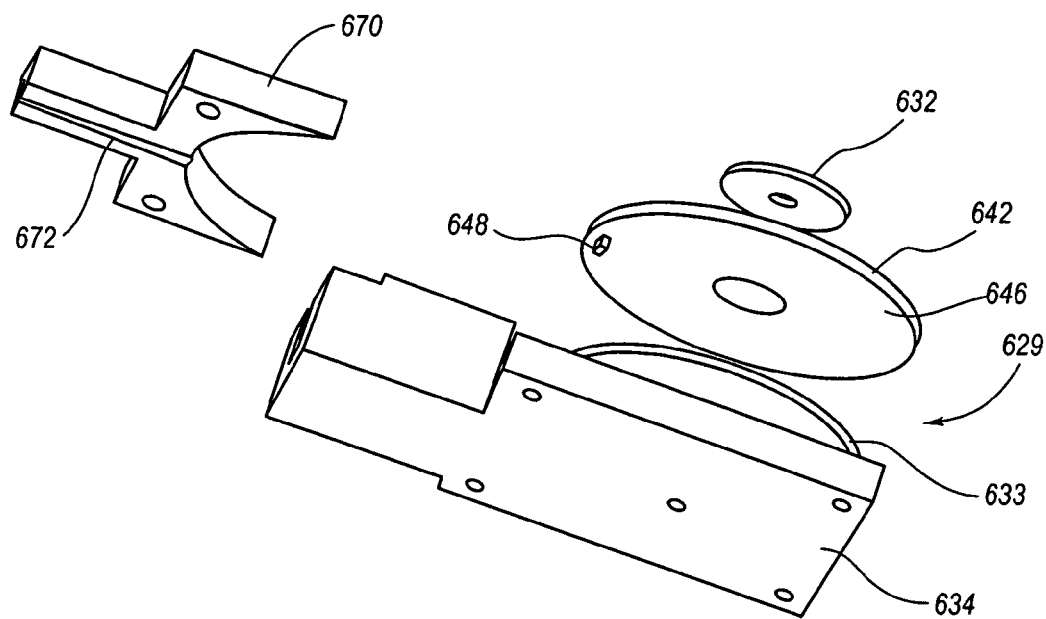
FIG. 6 is illustrates one embodiment of the driving mechanism of FIG. 5A in a bottom perspective assembly view according to the present invention.

According to FIGS. 5A and 6, the coil assembly 629 comprises a coil 633 having a first end 635. The coil 633 is operatively connected to the sealing plug 210 to automatically tamp the sealing plug 210 toward the anchor 208. The coil 633 may abut the tamping tube 212, or the coil 633 may comprise the tamping tube 212. The coil 633 may be semi-flexible and is capable of taking the shape of a track and also providing a compression force to the sealing plug 210.

The coil assembly 629 may further comprise a block such as plate block 634 that is disposed in the housing 252. The plate block 634 may comprise a generally planar first surface 636 that is receptive of a least a portion of the coil 633. The plate block 634 may thus include a channel such as a curved channel 638 shaped similarly to the coil 633 and may be recessed sufficiently to entirely receive the coil 633. The curved channel 638 may, however, exhibit a generally straight portion 639 as it leads out of the block 634. The plate block 634 may also comprise a protrusion 640 receptive of other components of the automatic driving mechanism 630. For example, the plate block 634 may be receptive of a driving plate 642.

The driving plate 642 may comprise a disk or circular shape as shown, although the driving plate 642 may include other shapes as well. The driving plate 642 may be rotatably attached to the plate block 634 as shown. The driving plate 642 includes a first generally planar surface 644 (FIG. 5A) and a second generally planar surface 646 (FIG. 6). A drive pin 648 extends laterally or normally from the second generally planar surface 646. The radial position of the drive pin 648 corresponds to a radius of curvature of the curved channel 638.

According to the embodiment of FIGS. 5A and 6, the drive pin 648 is rigidly fixed to or unitarily formed with the driving plate 642. When the automatic driving mechanism 630 is assembled, the drive pin 648 extends into the curved channel 638 adjacent to the first end 635 of the coil 633. Therefore, when the driving plate 642 rotates, the drive pin 648 engages or contacts the first end 635 of the coil 633 and provides a driving force to move a distal tip of the coil 633 along and out of the curved channel 638. The coil 633 is arranged adjacent to (or may even comprise) the tamping tube 212, and therefore advancing the coil 633 by the drive pin 648 may effect tamping of the sealing plug 210.

As shown in FIG. 5A, the driving plate 642 may be connected to a spool 632. The suture 204 is connected to and partially wound about the spool 632. The driving plate 642 tends to rotate at the same angular rate as the spool 632, however, a clutch 650 may selectively connect and release the driving plate 642 from the spool 632. One embodiment of the clutch 650 is described in detail below, however, any clutch may be used.

Withdrawal of the closure device 200 (FIG. 5F) from the tissue puncture site 218 (if the anchor 208 (FIG. 5F) is deployed and the automatic driving mechanism 630 has contacted the stop) causes the suture 204 to unwind from the spool 632. The spool 632 rotates as the suture 204 unwinds and provides a torsional motive force that is transduced to a linear tamping force.

The torsional motive force provided by the spool 632 is transduced into the linear tamping force by the coil assembly 629 according to the embodiment of FIGS. 5A and 6. The coil assembly 629 includes the coil 633 and the driving plate 642 arranged coaxially with the spool 632. When the spool 632 rotates, it drives the driving plate 642, which in turn drives the coil 633. The coil drives the tamping tube 212, which in turn tamps the sealing plug 210.

The tamping tube 212 is preferably tubular or semi-tubular partially disposed about the suture 204 along its longitudinal axis. If the coil 633 also comprises the tamping tube, the coil 633 may comprise a semi-tubular shape having a generally U-shaped cross section, to provide a trough through which the suture 204 may enter and exit laterally. An open trough would permit the suture and the coil 633 to merge as the spool 632 unwinds. Accordingly, with the anchor 208 deployed, as the closure device 200 is retracted in a first direction, the suture 204 unwinds from the spool 632, which drives the driving plate 642. The driving plate 642 drives the coil 633, and the coil 633 drives the tamping tube 212 in a second, opposite direction. The tamping tube tamps the sealing plug 210.

In embodiments including a clutch, the clutch 650 may comprise a plurality of release fingers 661 as shown in FIG. 5A. The release fingers 661 are arranged substantially in a circle. A first component 663 of the release fingers 661 is cantilevered from a base 637 and extends normal therefrom. A protrusion 665 of the first component 663 extends radially outward and is received by a mating internal recess 667 of the spool 632. A second component 669 of the release fingers 661 arcs substantially normal to the first component 663 and the base 637. The second component 669 of each of the release fingers 661 extends through a central hole 671 of the spool 632. An actuator button 651 fits over and contacts the second components 669 of each of the release fingers 661.

The fit of the protrusions 665 of the base 637 with the mating recesses 667 of the spool 632 causes the base 637 (and thus the driving plate 642 to which the base 637 is fixedly attached) and spool 632 to rotate together at an identical angular velocity. However, when the actuator button 651 is depressed, the actuator button slides along the arcs of the second component 669, forcing each of the release fingers 661 radially inward. The radial inward displacement of the release fingers 661 at least partially removes the protrusions 665 from the mating recesses 667, allowing independent rotation of the spool 632 with respect to the driving plate 642. Therefore, after the sealing plug 210 is driven toward the anchor 208, the selectably disengagable automatic driving mechanism 630 is disengaged or disabled, allowing the suture 204 to safely unwind without further tamping. The suture 204 is then exposed to the operator for convenient cutting.

As shown in FIGS. 5A and 6, the block 634 may also be receptive of a closing mold 670. The closing mold 670 matingly fits over the block 634 and provides a suture and coil path 672 therethrough leading to the carrier tube 202.

Figure 7:
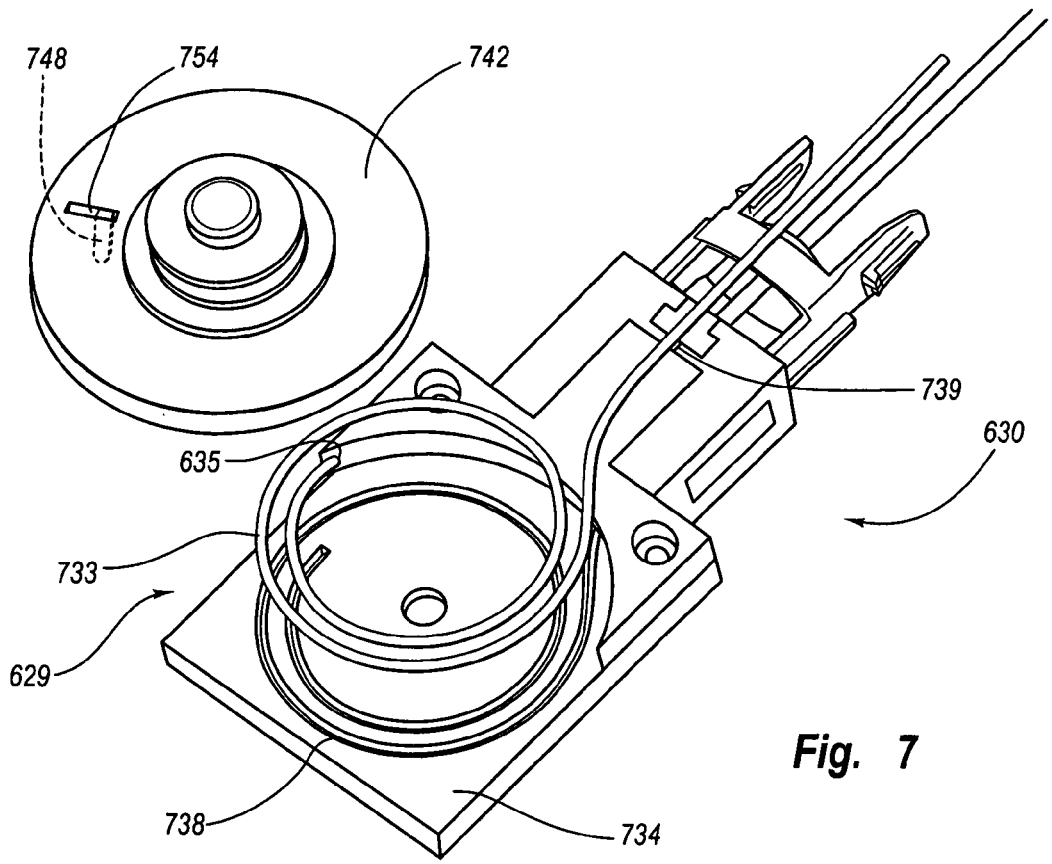
FIG. 7 illustrates another embodiment of a driving mechanism in a top assembly view according to one embodiment of the present invention.

Another embodiment of the automatic driving mechanism 630 is illustrated in FIG. 7. The automatic driving mechanism 630 of FIG. 7 may replace the mechanism 630 of FIG. 5A. The automatic driving mechanism 630 of FIG. 7 is similar to the embodiment of FIG. 5A, however, the coil assembly 629 of FIG. 7 comprises a spiral shaped coil 733. The spiral shaped coil 733 is operatively connected to the sealing plug 210 (FIG. 5A) to automatically tamp the sealing plug 210 (FIG. 5A) toward the anchor 208 (FIG. 5).

In addition, as shown in FIG. 7, block 734 may comprise a spiral channel 738 shaped like the spiral shaped coil 733. The spiral channel 738 may, however, exhibit a generally straight portion 739 as it leads out of the block 734. Driving plate 742 may be rotatably attached to the block 734. The driving plate 742 comprises, however, a radial slot 754 in which a sliding drive pin 748 rides. The sliding drive pin 748 extends normally from the driving plate 742 and into the spiral channel 738 at a first end 635 of the spiral coil 733. The sliding drive pin 748 is radially free floating in the slot 754, and it is angularly stable. Therefore, as the driving plate 742 rotates, the sliding drive pin 748 advances the spiral coil 733 along the spiral channel 738, and the sliding drive pin 748 slides radially to remain in the spiral channel 738 while continuing to advance the spiral coil 733. The spiral coil 733 effects tamping of the sealing plug 210 (FIG. 5A). The remaining components of the automatic driving mechanism 630 may be similar or identical to the embodiment of FIG. 5A.

Figure 8:
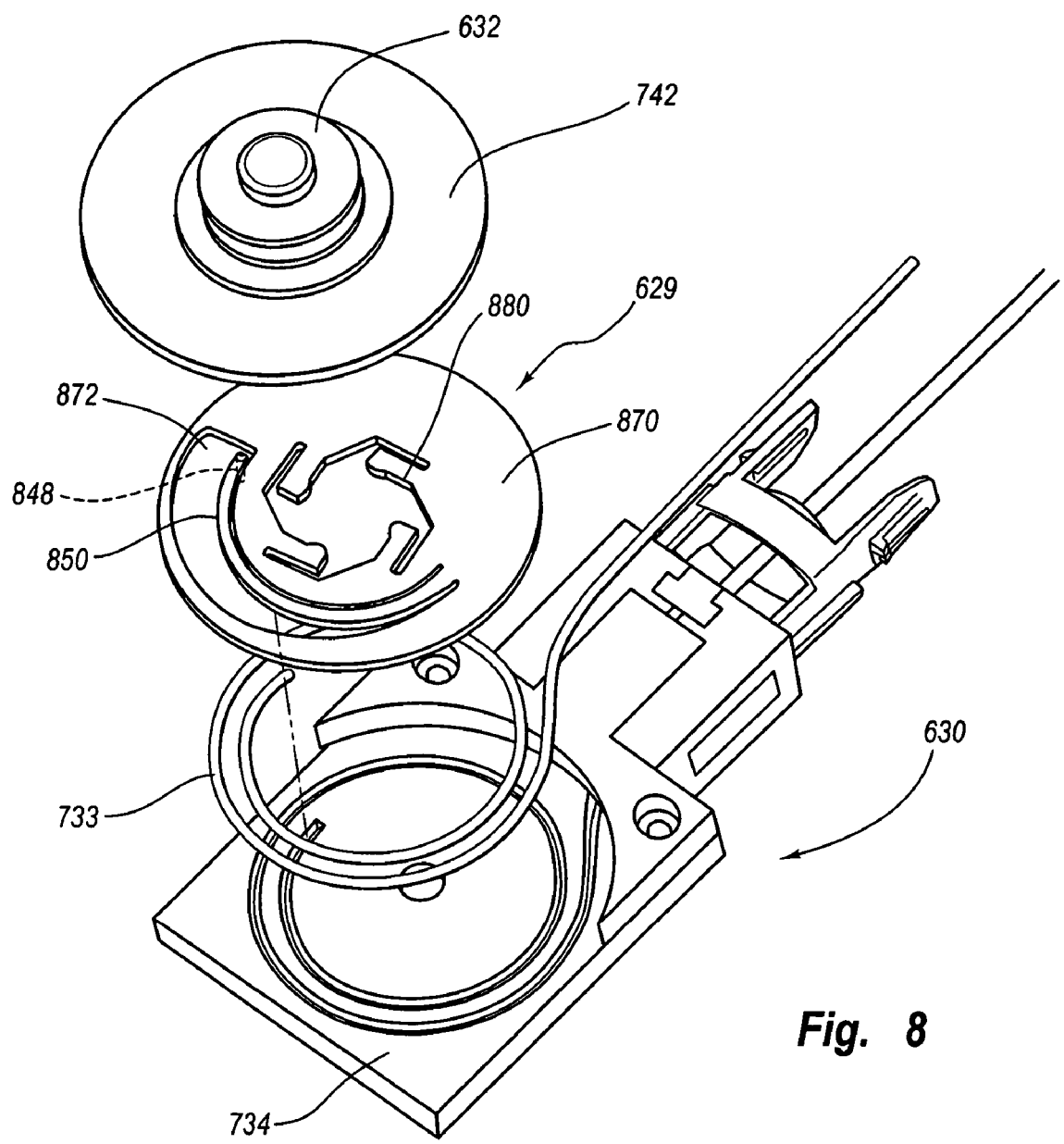
FIG. 8 illustrates another embodiment of a driving mechanism in a top assembly view according to one embodiment of the present invention.

Another embodiment of an automatic driving mechanism 630 is illustrated in FIG. 8. The automatic driving mechanism 630 of FIG. 8 may replace the mechanism 630 of FIG. 5A. The automatic driving mechanism 630 of FIG. 8 is similar to the embodiment of FIG. 7, however, the coil assembly 629 of FIG. 8 comprises a disk such as a compliant plate 870. The compliant plate 870 is fixed to the driving plate 742, but may also be clutched thereto with a spiral connection 880. The compliant plate 870 comprises an open slit 872 of variable width and a cantilevered finger 850 coplanar with the compliant plate 870 and extending along the open slit 872. The cantilevered finger 850 is radially flexible within the open slit 872 and includes a lateral drive pin 848 at a distal end thereof. The drive pin 848 is thus free to move radially within the open slit 872, and it is angularly stable. Therefore, as the driving plate 742 rotates, it drives the compliant plate 870, and the compliant plate 870 comprising the drive pin 848 advances the spiral coil 733 along the spiral channel 738. The drive pin 848 moves radially as the compliant plate 870 rotates to remain in the spiral channel 738 while continuing to advance the spiral coil 733, and the spiral coil 733 effects tamping of the sealing plug 210 (FIG. 5A). According to some embodiments, the compliant plate 870 also comprises a driving plate and the driving plate 742 may be omitted. The remaining components of the automatic driving mechanism 630 may be similar or identical to the embodiment of FIG. 5A.

It will be understood by those of skill in the art having the benefit of this disclosure that the coil assembly 629 configurations shown in FIGS. 5A, 6, 7, and 8 are exemplary in nature, and not limiting. Any configuration may be used to advance a coil within a channel to provide an automatic driving force to the sealing plug 210 (FIG. 5F).

Operation of the embodiment of FIGS. 5A-8 is as follows. As the handle 252 of the closing device 200 is retracted from the puncture tract 219 as shown in FIG. 5B, the detent 255 releases. The automatic tamping mechanism 630 and carrier tube 202 may remain stationary and therefore float relative to the handle 252. The procedure sheath 216 is retracted as the handle 252 is withdrawn, exposing the distal end 207 of the carrier tube 202. The automatic tamping mechanism 630 eventually contacts a stop (or, in some embodiments, the automatic tamping mechanism is fixed), and further retraction causes the automatic tamping mechanism 630 and carrier tube 202 to retract as well. As the automatic tamping mechanism 630 retracts, the suture 204, which is threaded through the anchor 208, unwinds from and causes rotation of the spool 632. The spool 632 drives the driving plate 642/742 or the compliant plate 870 as it rotates via a coaxial connection between. As the driving plate 642/742 and/or the compliant plate 870 rotate, the coil 633/733 is advanced along the channel 638/738. The coil 633/733 drives the tamping tube 212, or the coil 633/733 may be long enough to operate as a tamping tube itself. The tamping tube 212 tamps the sealing plug 210. According to spiral or non-circular coil designs, the drive pin 748 of the driving plate 742 or the drive pin 848 of compliant plate 870 may migrate radially to remain in the spiral channel 738 and advance the coil 733.

Therefore, as the closing device 200 is retracted from the puncture tract 219, the procedure sheath 216 may be retracted (FIGS. 5D-5E), and the sealing plug 210 is automatically tamped (FIGS. 5F-5G). The sealing plug 210 is more likely to create a sufficient arterial seal without a gap relative to the anchor 208, as may otherwise occur with a separate manual tamping procedure.

Moreover, when the sealing plug 210 has been sufficiently tamped, the automatic driving mechanism 630 may be disengaged, enabling further retraction of the closure device 200 without additional tamping. With the sealing plug 210 fully tamped, there may be little or no portion of the suture 204 extending outside of the tissue layer 230 and exposed to an operator. Therefore, it may be difficult for an operator to separate the sealing plug 210 and anchor 208 from the remainder of the closure device 200. In addition, too much retraction with the selectably automatic driving mechanism 630 enabled could potentially overtamp the sealing plug 210 into the artery 228. Accordingly, the automatic driving mechanism 630 may be advantageously disabled by activating the actuator 651 through the access hole 253. Activating the actuator 651 allows the suture 204 to fully unwind from the spool 632 without driving the tamping tube 212. Unwinding the spool 632 exposes a sufficient length of the suture 204 to allow an operator to easily cut it and separate the sealing plug 210 and anchor 208 from the remainder of the closure device 200.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. An apparatus, comprising:
   a tissue puncture closure device, the tissue puncture closure device comprising:
   an anchor;
   a sealing plug;
   a connector slidingly attaching the sealing plug to the anchor;
   a tamping tube disposed adjacent the sealing plug;
   a coil structured and arranged to apply an axially directed compressive force to the tamping tube to drive the tamping tube to automatically tamp the sealing plug toward the anchor, the coil having a distal end and a proximal end;
   a driving plate arranged to contact and apply a force to the proximal end of the coil upon rotation of the driving plate to advance a distal tip of the distal end of the coil.

2. An apparatus according to claim 1 wherein the tamping tube abuts the coil or the coil comprises the tamping tube.

3. An apparatus according to claim 1 wherein the tissue puncture closure device further comprises:
   a housing;
   a block disposed in the housing and receptive of at least a portion of the coil;
   the driving plate adjacent to the coil.

4. An apparatus according to claim 1 wherein the tissue puncture closure device further comprises:
   a housing;
   a block disposed in the housing comprising a curved channel receptive of at least a portion of the coil;
   the driving plate rotatably attached to the block, the driving plate comprising a drive pin extending into the curved channel adjacent to the proximal end of the coil.

5. An apparatus according to claim 1 wherein the connector comprises a filament, and wherein the tissue puncture closure device further comprises:
   a housing;
   a block disposed in the housing comprising a curved channel receptive of at least a portion of the coil;
   the driving plate rotatably attached to the block, the driving plate comprising a drive pin extending into the curved channel adjacent to the proximal end of the coil;
   a spool connected to the driving plate, wherein a portion of the filament is wound around the spool.

6. An apparatus according to claim 1 wherein the connector comprises a filament, and wherein the tissue puncture closure device further comprises:
   a housing;
   a block disposed in the housing comprising a curved channel receptive of at least a portion of the coil;
   the driving plate rotatably attached to the block, the driving plate comprising a drive pin extending into the curved channel adjacent to the proximal end of the coil;
   a spool connected by a releasable clutch to the driving plate, wherein a portion of the filament is wound around the spool.

7. An apparatus according to claim 1 wherein the tissue puncture closure device further comprises:
   a housing;
   a block disposed in the housing comprising a spiraled channel receptive of at least a portion of the coil;
   the driving plate rotatably attached to the block, the driving plate comprising a drive pin extending into the spiraled channel adjacent to the proximal end of the coil.

8. An apparatus according to claim 1 wherein the tissue puncture closure device further comprises:
   a housing;
   a block disposed in the housing comprising a spiraled channel receptive of at least a portion of the coil;
   the driving plate rotatably attached to the block, the driving plate comprising a radially free floating, angularly stable drive pin extending into the spiraled channel adjacent to the proximal end of the coil.

9. An apparatus according to claim 1 wherein the tissue puncture closure device further comprises:
   a housing;
   a block disposed in the housing comprising a spiraled channel receptive of at least a portion of the coil;
   the driving plate rotatably attached to the block, the driving plate comprising a radially compliant, angularly stable drive pin extending into the spiraled channel adjacent to the proximal end of the coil.

10. An apparatus according to claim 1 wherein the connector comprises a filament, and wherein the tissue puncture closure device further comprises:
    a housing;
    a block disposed in the housing comprising a curved channel portion leading to a straight channel portion, the curved and straight channel portions receptive of at least a portion of the coil;
    the driving plate rotatably attached to the block, the driving plate comprising a drive pin extending into the curved channel adjacent to the proximal end of the coil;
    a spool connected by a releasable clutch to the driving plate, wherein a portion of the filament is wound around the spool.

11. An apparatus according to claim 1 wherein the coil is driven by a selectably disengagable automatic driving mechanism to tamp the sealing plug;
    wherein the selectably disengagable automatic driving mechanism comprises a transducer for effecting a tamping force on the sealing plug via the coil upon withdrawal of the closure device from the tissue wall puncture.

12. A tissue puncture closure device for partial insertion into and sealing of a tissue puncture in an internal tissue wall accessible through a percutaneous incision, comprising:
    an anchor for disposition on a distal side of the internal tissue wall;

a sealing plug for disposition on a proximal side of the internal tissue wall;
a filament connected to and anchored at a distal end to the anchor and sealing plug for slidably cinching the anchor and sealing plug together about the tissue puncture, wherein the sealing plug is slidably disposed on the filament proximal to the anchor;
a tamping device disposed on the filament for driving the sealing plug along the filament distally towards the anchor;
a storage spool onto which a proximal end of the filament is wound;
a driving plate connected to the storage spool;
a coil structured and arranged to apply an axially directed compressive force to the tamping device to drive the tamping device to tamp the sealing plug, the coil having a distal end and a proximal end;
wherein the driving plate is arranged to contact and apply a force to the proximal end of the coil structure upon rotation of the driving plate to advance a distal tip of the distal end of the coil structure.

13. A tissue puncture closure device for partial insertion into and sealing of a tissue puncture in an internal tissue wall accessible through a percutaneous incision according to claim 12 wherein the driving plate is connected to the storage spool by a releasable clutch.

14. A tissue puncture closure device for partial insertion into and sealing of a tissue puncture in an internal tissue wall accessible through a percutaneous incision according to claim 12, further comprising:
a housing;
a block disposed in the housing comprising a curved channel receptive of at least a portion of the coil;
wherein the driving plate is rotatably attached to the block, the driving plate comprising a drive pin extending into the curved channel adjacent to the proximal end of the coil.

15. A tissue puncture closure device for partial insertion into and sealing of a tissue puncture in an internal tissue wall accessible through a percutaneous incision according to claim 12, further comprising:
a housing;
a block disposed in the housing comprising a spiraled channel receptive of at least a portion of the coil;
wherein the driving plate is rotatably disposed adjacent to the block, the driving plate comprising a radially floating, angularly stable drive pin extending into the spiraled channel adjacent to the proximal end of the coil.

16. A tissue puncture closure device for partial insertion into and sealing of a tissue puncture in an internal tissue wall accessible through a percutaneous incision according to claim 12, further comprising:
a housing;
a block disposed in the housing comprising a spiraled channel receptive of at least a portion of the coil;
wherein the driving plate comprises:
a disk rotatably attached to the block;
a slit in the disk;
a radially flexible cantilevered finger in the slit having a drive pin extending laterally into the spiraled channel at the proximal end of the coil.

17. A tissue puncture closure device for partial insertion into and sealing of a tissue puncture in an internal tissue wall accessible through a percutaneous incision according to claim 12 wherein the coil also comprises the tamping device.

18. A tissue puncture closure device for partial insertion into and sealing of a tissue puncture in an internal tissue wall accessible through a percutaneous incision according to claim 12 wherein withdrawal of the closure device from the tissue puncture with the anchor bearing against the internal tissue wall unwinds the filament from the storage spool, wherein the storage spool rotates the driving plate, and the driving plate drives the coil to directly or indirectly provide a tamping force to the sealing plug.

19. A tissue puncture closure device for partial insertion into and sealing of a tissue puncture in an internal tissue wall accessible through a percutaneous incision according to claim 12 wherein the coil is at least partially coiled about an axis arranged coaxial with an axis of rotation of the storage spool.

* * * * *